(12) United States Patent
Steadman et al.

(10) Patent No.: US 11,587,408 B2
(45) Date of Patent: Feb. 21, 2023

(54) CURRENCY DISINFECTING ASSEMBLY

(71) Applicants: John Steadman, Jefferson, OH (US); Lynn Egensperger, Jefferson, OH (US)

(72) Inventors: John Steadman, Jefferson, OH (US); Lynn Egensperger, Jefferson, OH (US)

( * ) Notice: Subject to any disclaimer, the term of this patent is extended or adjusted under 35 U.S.C. 154(b) by 61 days.

(21) Appl. No.: 17/029,897

(22) Filed: Sep. 23, 2020

(65) Prior Publication Data
US 2022/0092947 A1 Mar. 24, 2022

(51) Int. Cl.
| | |
|---|---|
| *G07F 19/00* | (2006.01) |
| *A61L 2/10* | (2006.01) |
| *A61L 2/26* | (2006.01) |
| *G16H 40/63* | (2018.01) |
| *G06Q 20/10* | (2012.01) |
| *G06F 3/0488* | (2022.01) |
| *G06F 3/04847* | (2022.01) |

(52) U.S. Cl.
CPC .............. *G07F 19/203* (2013.01); *A61L 2/10* (2013.01); *A61L 2/26* (2013.01); *G06Q 20/1085* (2013.01); *G16H 40/63* (2018.01); *A61L 2202/11* (2013.01); *A61L 2202/14* (2013.01); *G06F 3/0488* (2013.01); *G06F 3/04847* (2013.01)

(58) Field of Classification Search
CPC ...................... G06Q 20/1085; H01H 2231/006
USPC .......................... 235/7 R, 2, 375, 235; 705/43
See application file for complete search history.

(56) References Cited

U.S. PATENT DOCUMENTS

| | | | |
|---|---|---|---|
| 4,449,050 A | 5/1984 | Kamhi | |
| 7,658,321 B1 | 2/2010 | Green | |
| 2005/0035034 A1* | 2/2005 | Long | G07D 11/50 |
| | | | 209/534 |
| 2021/0366244 A1* | 11/2021 | Denny | G07F 19/201 |

FOREIGN PATENT DOCUMENTS

| | | | | |
|---|---|---|---|---|
| CN | 1478553 A | * | 3/2004 | |
| CN | 213690788 U | * | 7/2021 | |
| JP | H0765216 A | * | 3/1995 | |
| KR | 910014857 | | 8/1991 | |
| KR | 100954228 B1 | * | 4/2010 | |
| KR | 20110043028 A | * | 4/2011 | ......... G07D 11/0084 |
| KR | 101095351 B1 | * | 12/2011 | ............. A61L 2/025 |
| KR | 101545608 B1 | * | 6/2014 | |
| KR | 200478413 | | 10/2015 | |
| WO | WO-2005098763 A2 | * | 10/2005 | ............. A61L 2/025 |

* cited by examiner

*Primary Examiner* — Edwyn Labaze

(57) ABSTRACT

A currency disinfecting assembly includes a housing that has entry extending therein and an exit extending to receive and dispense paper currency. A roller unit is positioned in the housing and the roller unit is positioned between the entry and the exit to transport the paper currency between the entry and the exit. A disinfecting unit is integrated into the housing and the disinfecting unit emits electromagnetic radiation to kill bacteria. A control unit is coupled to the housing and the control unit is in communication with the roller unit and the disinfecting unit. Moreover, the control unit turns on each of the roller unit and the disinfecting unit to facilitate the user to sterilize their paper currency.

13 Claims, 5 Drawing Sheets

CURRENCY DISINFECTING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to disinfecting devices and more particularly pertains to a new disinfecting device for disinfecting paper currency.

(2) Description of Related Art Including Information Disclosed Under 37 CFR 1.97 and 1.98

The prior art relates to disinfecting devices including a variety of sterilizing devices that dispense and sterilize paper currency using ultraviolet light. The prior art discloses a feeder device for paper currency that employs motorized rollers. Additionally, the prior art discloses an automated teller machine that employs disinfecting techniques to disinfect control surfaces on the automated teller machine.

BRIEF SUMMARY OF THE INVENTION

An embodiment of the disclosure meets the needs presented above by generally comprising a housing that has entry extending therein and an exit extending to receive and dispense paper currency. A roller unit is positioned in the housing and the roller unit is positioned between the entry and the exit to transport the paper currency between the entry and the exit. A disinfecting unit is integrated into the housing and the disinfecting unit emits electromagnetic radiation to kill bacteria. A control unit is coupled to the housing and the control unit is in communication with the roller unit and the disinfecting unit. Moreover, the control unit turns on each of the roller unit and the disinfecting unit to facilitate the user to sterilize their paper currency.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
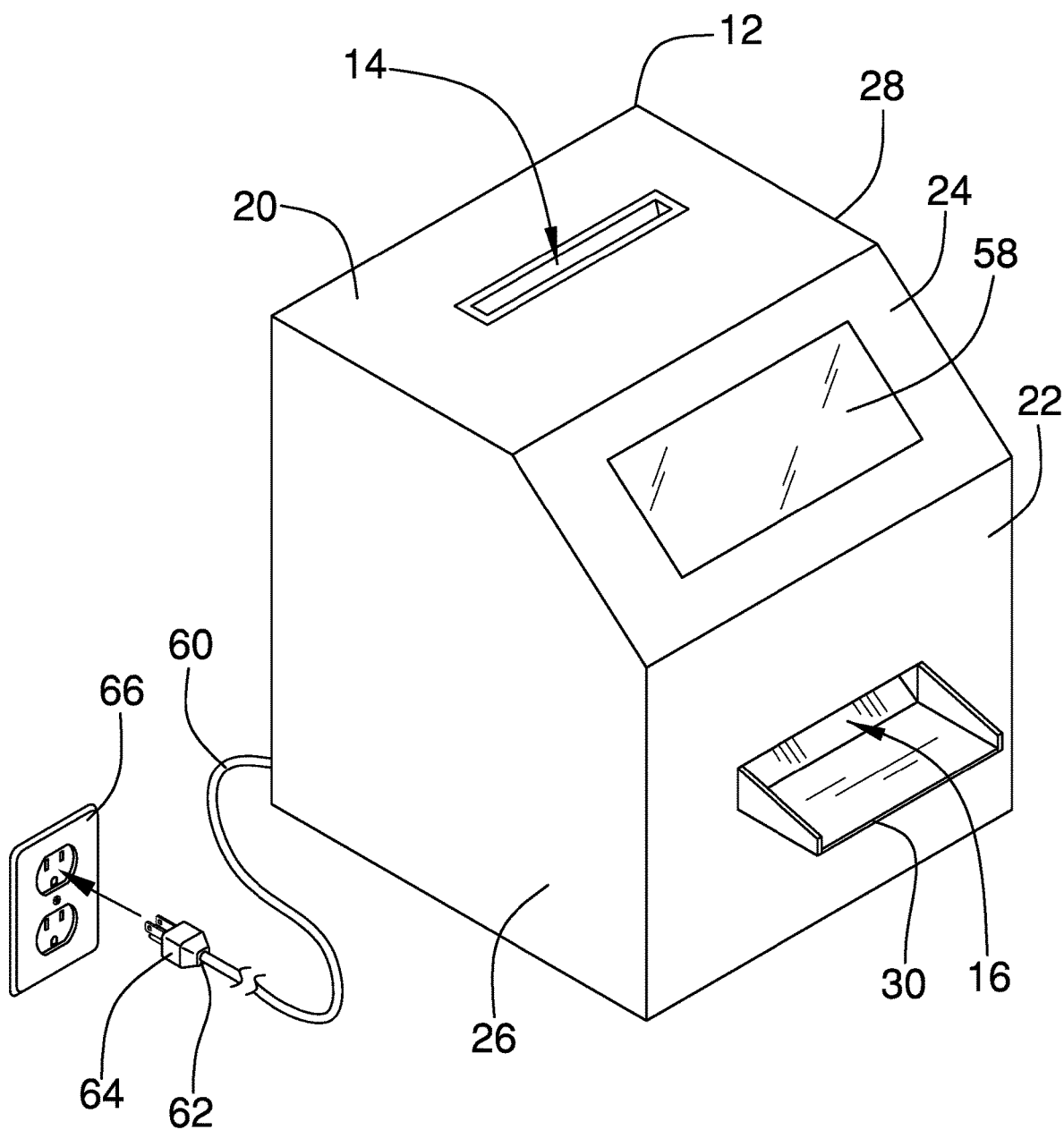
FIG. 1 is a perspective view of a currency disinfecting assembly according to an embodiment of the disclosure.
Figure 2:
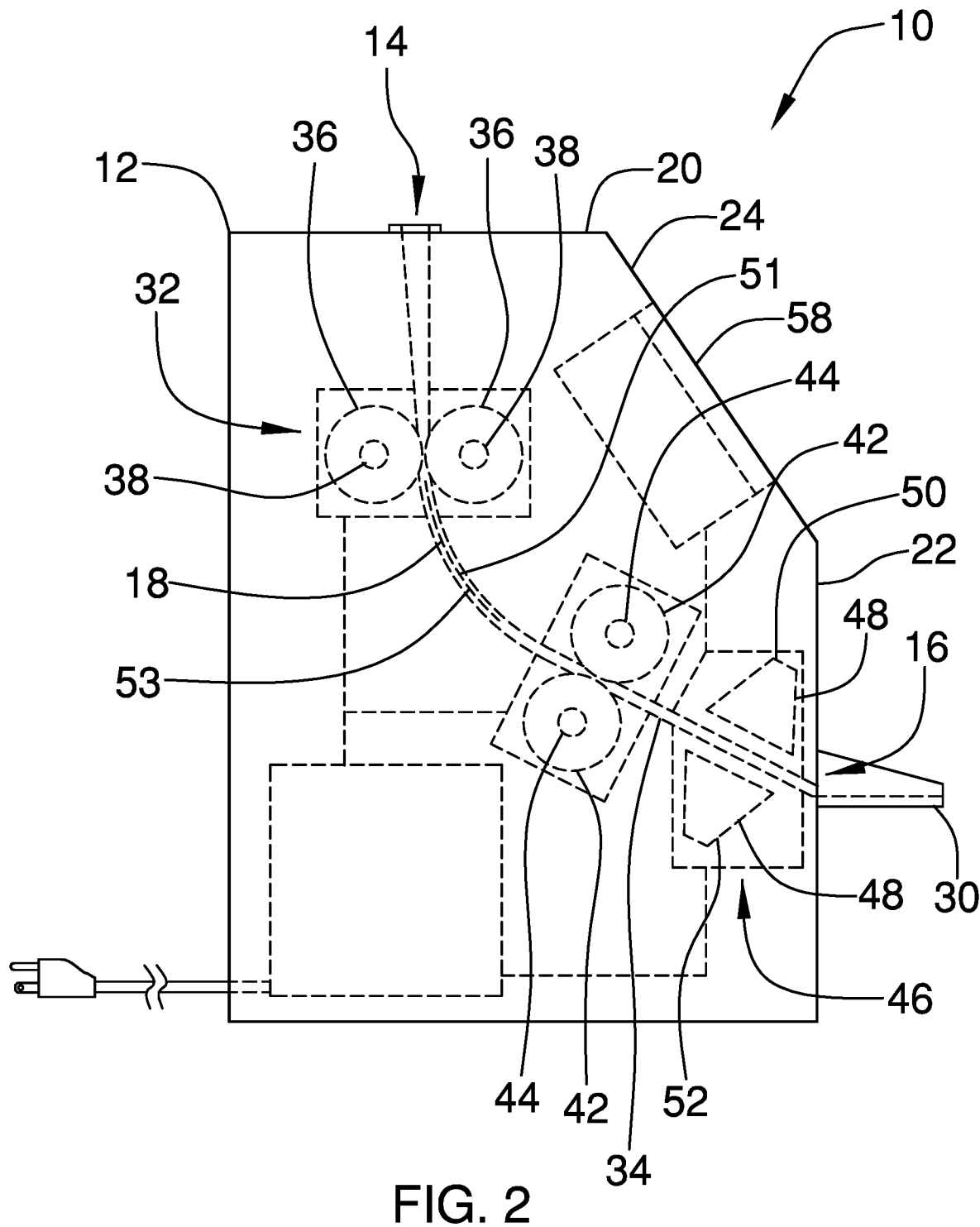
FIG. 2 is a right side phantom view of an embodiment of the disclosure.
Figure 3:
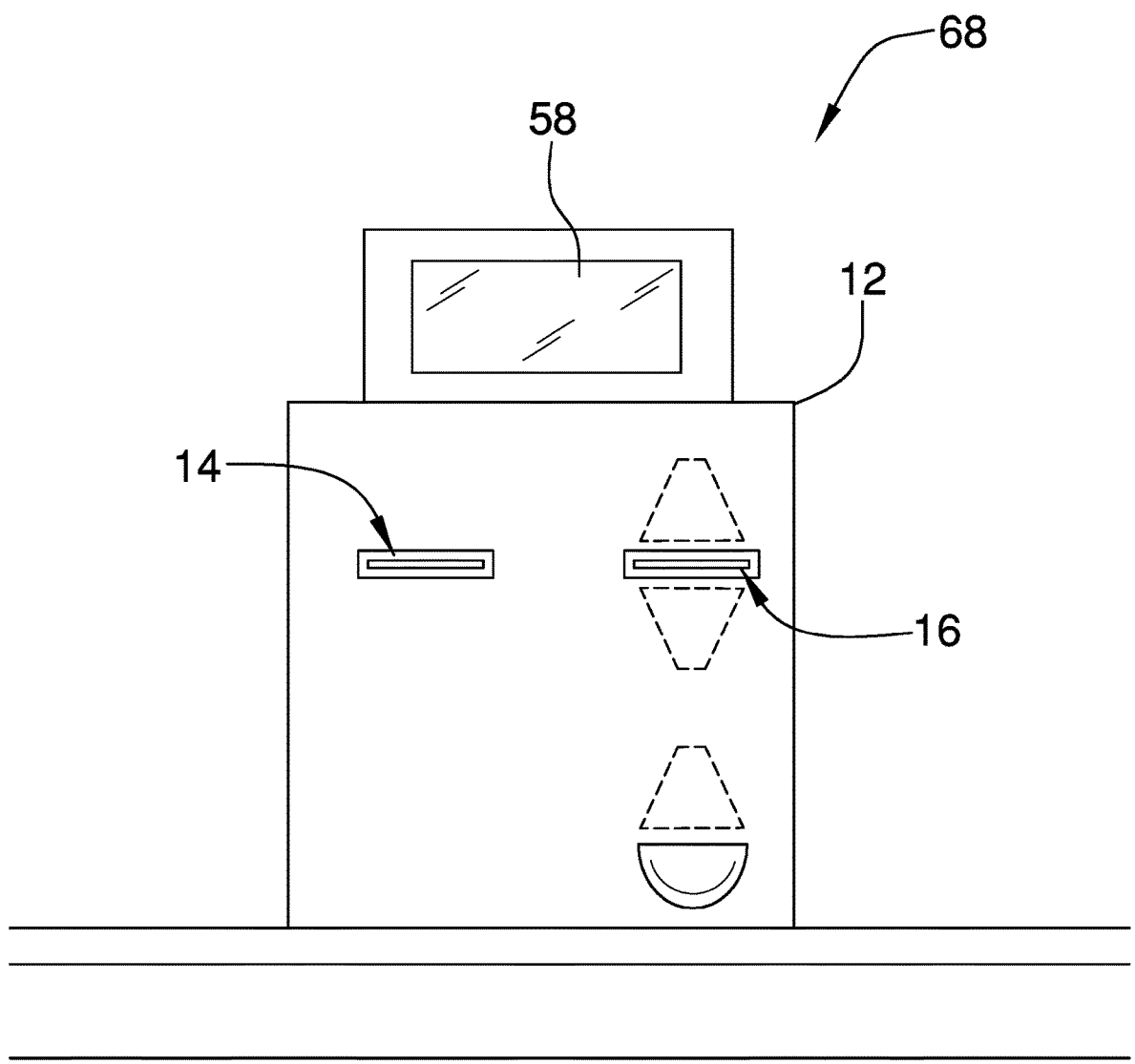
FIG. 3 is a front phantom view of an embodiment of the disclosure showing a housing as a cash register.
Figure 4:
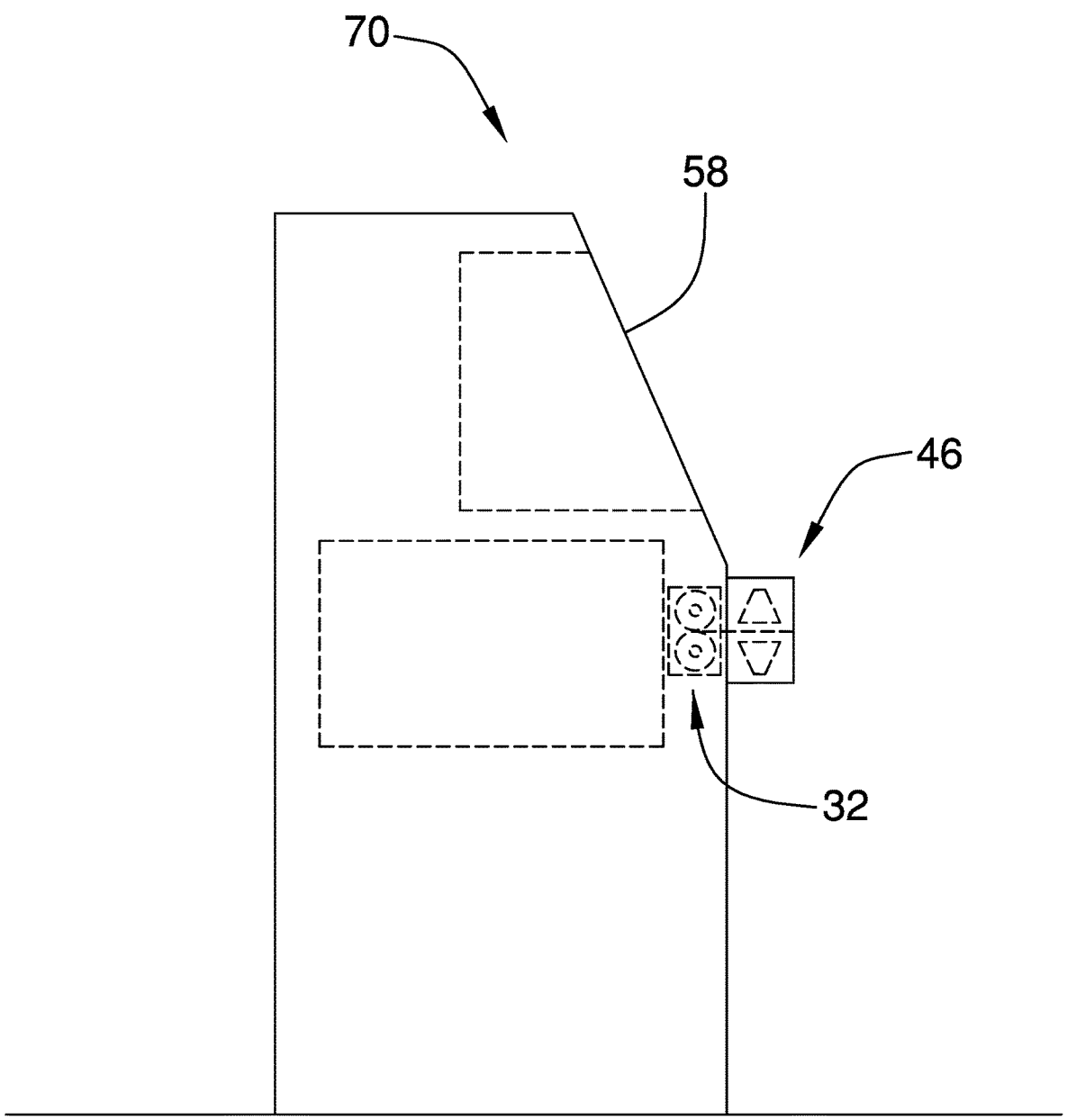
FIG. 4 is a right side phantom view of an embodiment of the disclosure showing a housing as an automated teller machine.
Figure 5:
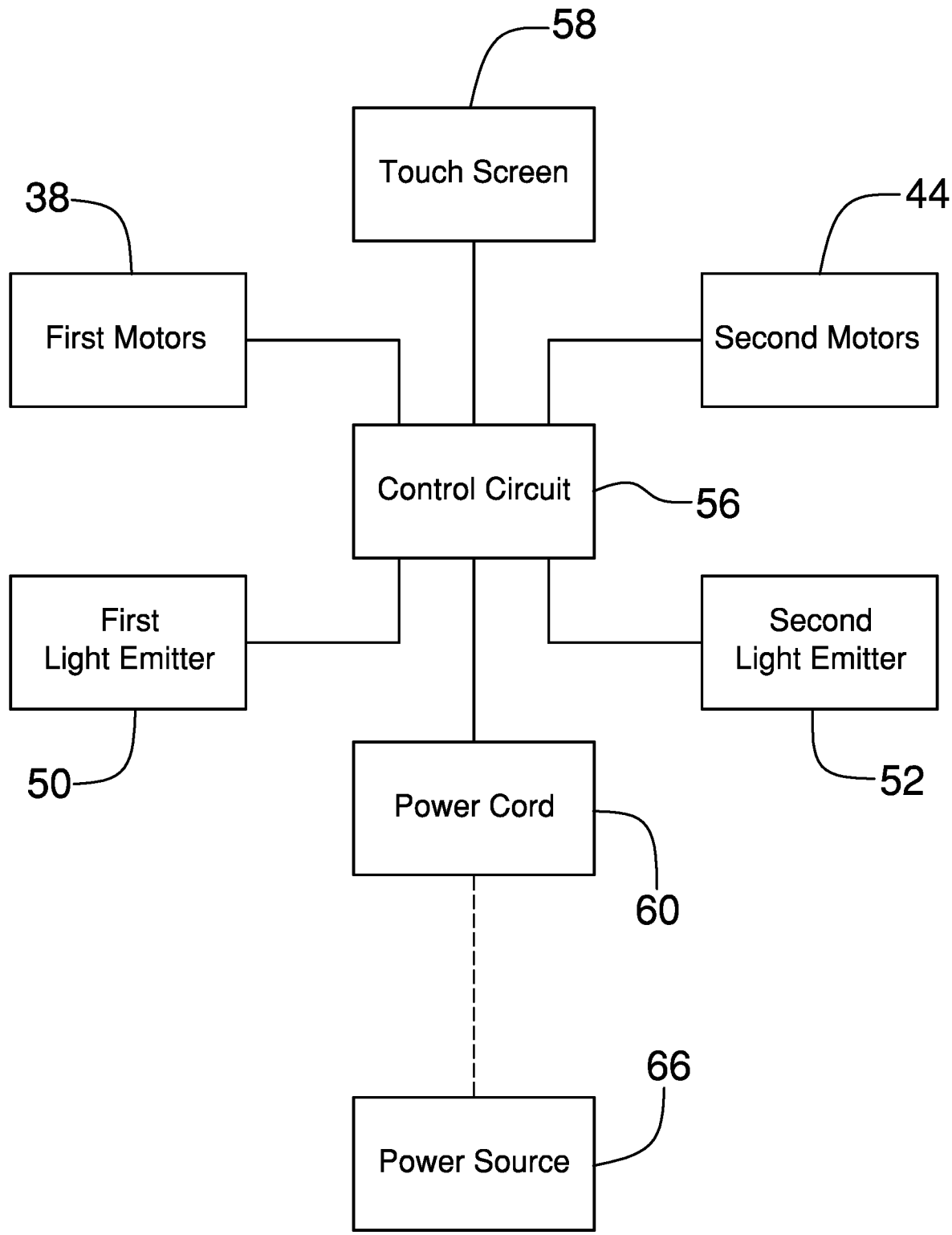
FIG. 5 is a schematic view of an embodiment of the disclosure.

With reference now to the drawings, and in particular to FIGS. 1 through 5 thereof, a new disinfecting device embodying the principles and concepts of an embodiment of the disclosure and generally designated by the reference numeral 10 will be described.

As best illustrated in FIGS. 1 through 5, the currency disinfecting assembly 10 generally comprises a housing 12 that has an entry 14 extending therein and an exit 16 extending therein. The entry 14 receives paper currency 18 and the exit 16 dispenses the paper currency 18. The housing 12 has a top wall 20, a front wall 22 and an angled wall 24 sloping between the front wall 22 and the top wall 20. Additionally, the housing 12 has a first lateral wall 26 and a second lateral wall 28. The entry 14 extends through the top wall 20 and the exit 16 extends through the front wall 22. A chute 30 is coupled to the front wall 22 of the housing 12 and the chute 30 is aligned with the exit 16 to dispense the paper currency 18.

A roller unit 32 is provided and the roller unit 32 is positioned in the housing 12. The roller unit 32 is positioned between the entry 14 and the exit 16 to facilitate the roller unit 32 to engage the paper currency 18. The roller unit 32 is actuatable in a rolling condition to transport the paper currency 18 between the entry 14 and the exit 16. The roller unit 32 comprises a passageway 34 that is integrated into the housing 12 and the passageway 34 extends between the entry 14 and the exit 16 to transport the paper currency 18.

The roller unit 32 includes a pair of first rollers 36 and each of the first rollers 36 is rotatably positioned in the housing 12. Each of the first rollers 36 extends between the first lateral wall 26 and the second lateral wall 28. Each of the first rollers 36 is positioned on opposing sides of the passageway 34 from each other to frictionally engage the paper currency 18. Each of the first rollers 36 is positioned closer to the entry 14 than the exit 16. The roller unit 32 includes a pair of first motors 38 and each of the first motors 38 is coupled to a respective one of the first rollers 36. Each of the first motors 38 rotates the respective first roller 36 in a first direction when the first motors 38 are turned on for transporting the paper currency 18 through the passageway 34. Each of the first motors 38 may comprise an electric motor or the like.

The roller unit 32 includes a pair of second rollers 42 and each of the second rollers 42 is rotatably positioned in the housing 12. Each of the second rollers 42 extends between the first lateral wall 26 and the second lateral wall 28. Additionally, each of the second rollers 42 is positioned on opposing sides of the passageway 34 from each other to frictionally engage the paper currency 18. Each of the second rollers 42 is positioned closer to the exit 16 than the entry 14. The roller unit 32 includes a pair of second motors 44 and each of the second motors 44 is coupled to a respective one of the second rollers 42. Each of the second motors 44 rotates the respective second roller 42 in a first direction when the second motors 44 are turned on for transporting the paper currency 18 through the passageway 34. Each of the second motors 44 may comprise an electric motor or the like.

A disinfecting unit 46 is provided and the disinfecting unit 46 is integrated into the housing 12. The disinfecting unit 46 emits electromagnetic radiation at a frequency known to kill bacteria. Additionally, the disinfecting unit 46 includes a plurality of emitters 48 that is each directed toward opposing sides of the roller unit 32 to disinfect both sides of the paper currency 18 as the paper currency 18 is transported through the housing 12. In this way the paper currency 18 is completely sterilized thereby inhibiting the paper currency 18 from transferring bacteria to a user.

The plurality of emitters 48 includes a first light emitter 50 that is positioned in the housing 12. The first light emitter 50 is directed downwardly toward the passageway 34 to emit ultraviolet light onto a top surface 51 of the paper currency 18 for sterilizing the top surface 51 of the paper currency 18. The first light emitter 50 is positioned between the second rollers 42 and the exit 16 in the housing 12. The plurality of emitters 48 includes a second light emitter 52 that is positioned in the housing 12. The second light emitter 52 is directed upwardly toward the passageway 34 to emit ultraviolet light onto a bottom surface 53 of the paper currency 18. The second light emitter 52 is aligned with the first light emitter 50. Additionally, each of the first light emitter 50 and the second light emitter 52 may emit ultraviolet light for killing the bacteria.

A control unit 54 is provided and the control unit 54 is coupled to the housing 12 and the control unit 54 is manipulated by a user. The control unit 54 is in communication with the roller unit 32 and the disinfecting unit 46. The control unit 54 turns on each of the roller unit 32 and the disinfecting unit 46 to facilitate the user to sterilize their paper currency 18. The control unit 54 comprises a control circuit 56 that is positioned in the housing 12. The control circuit 56 is electrically coupled to each of the first motors 38, the second motors 44, the first light emitter 50 and the second light emitter 52. The control circuit 56 receives a disinfect input and each of the first motors 38, the second motors 44, the first light emitter 50 and the second light emitter 52 is turned on when the control circuit 56 receives the disinfect input.

The control unit 54 includes a touch screen 58 that is coupled to the angled wall 24 of the housing 12 and the touch screen 58 can be manipulated by the user. The touch screen 58 is electrically coupled to the control circuit 56 and the touch screen 58 displays operational indicia to facilitate the user to control operational parameters of the control circuit 56. The control unit 54 includes a power cord 60 that is coupled to and extends away from the housing 12. The power cord 60 is electrically coupled to the control circuit 56 and the power cord 60 has a distal end 62 with respect to the housing 12. Additionally, a male plug 64 can be electrically coupled to a power source 66 comprising a female electrical outlet. As is most clearly shown in FIG. 3, the housing 12 may comprise a cash register 68 that is employed in a retail environment thereby facilitating change dispensed for a transaction to be sterilized. As is most clearly shown in FIG. 4, the housing 12 may comprise an automatic teller machine 70 at a bank or the like for sterilizing cash that is dispensed.

In use, the touch screen 58 is manipulated to turn on the disinfecting unit 46 and the roller unit 32 and the paper currency 18 is inserted into the entry 14. In this way the paper currency 18 is transported through the housing 12 to be sterilized prior to being dispensed outwardly through the exit 16. Thus, the paper currency 18 is sterilized to inhibit the transmission of bacteria from the paper currency 18 to the user. The paper currency 18 is thusly inhibited from participating in the transmission of Covid 19 or other pandemic related infectious diseases.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A currency disinfecting assembly for disinfecting paper currency, said assembly comprising:
   a housing having an entry extending therein and an exit extending therein wherein said entry is configured to receive paper currency and said exit is configured to dispense the paper currency;
   a roller unit being positioned in said housing, said roller unit being positioned between said entry and said exit wherein said roller unit is configured to engage the paper currency, said roller unit being actuatable in a rolling condition wherein said roller unit is configured to transport the paper currency between said entry and said exit;
   a disinfecting unit being integrated into said housing, said disinfecting unit emitting electromagnetic radiation wherein said disinfecting unit is configured to kill bacteria, said disinfecting unit including a plurality of emitters each being directed toward opposing sides of said roller unit wherein said disinfecting unit is configured to disinfect both sides of the paper currency as the paper currency is transported through said housing, said disinfecting unit being positioned and directed towards said roller unit adjacent to said exit of said housing wherein said disinfecting unit is configured for killing bacteria immediately prior to the paper currency being dispensed through said exit of said housing; and a control unit being coupled to said housing wherein said control unit is configured to be manipulated by a user, said control unit being in communication with said roller unit and said disinfecting unit, said control unit turning on each of said roller unit and said disinfecting unit wherein said control unit is configured to facilitate the user to sterilize their paper currency.

2. The assembly according to claim 1, wherein:
said housing has a top wall, a front wall, and an angled wall sloping between said front wall and said top wall, said housing having a first lateral wall and a second lateral wall, said entry extending through said top wall, said exit extending through said front wall; and
said assembly includes a chute being coupled to said front wall of said housing, said chute being aligned with said exit wherein said chute is configured to dispense the paper currency.

3. The assembly according to claim 1, wherein said roller unit comprises a passageway being integrated into said housing, said passageway extending between said entry and said exit wherein said passageway is configured to transport the paper currency.

4. The assembly according to claim 3, wherein said roller unit includes a pair of first rollers, each of said first rollers being rotatably positioned in said housing, each of said first rollers extending between a first lateral wall and a second lateral wall of said housing, each of said first rollers being positioned on opposing sides of said passageway from each other wherein each of said first rollers is configured to frictionally engage the paper currency, each of said first rollers being positioned closer to said entry than said exit.

5. The assembly according to claim 4, wherein said roller unit includes a pair of first motors, each of said first motors being coupled to a respective one of said first rollers, each of said first motors rotating said respective first roller in a first direction when said first motors are turned on for transporting the paper currency through said passageway.

6. The assembly according to claim 4, wherein said roller unit includes a pair of second rollers, each of said second rollers being rotatably positioned in said housing, each of said second rollers extending between said first lateral wall and said second lateral wall, each of said second rollers being positioned on opposing sides of said passageway from each other wherein each of said second rollers is configured to frictionally engage the paper currency, each of said second rollers being positioned closer to said exit than said entry.

7. The assembly according to claim 6, wherein:
said roller unit includes a pair of first motors; and
said roller unit includes a pair of second motors, each of said second motors being coupled to a respective one of said second rollers, each of said second motors rotating said respective second roller in a first direction when said second motors are turned on for transporting the paper currency through said passageway.

8. The assembly according to claim 6, wherein said disinfecting unit comprises a first light emitter being positioned in said housing, said first light emitter being directed downwardly toward said passageway wherein said first light emitter is configured to emit ultraviolet light onto a top surface of the paper currency for sterilizing the top surface of the paper currency, said first light emitter being positioned between said second rollers and said exit in said housing.

9. The assembly according to claim 8, wherein said disinfecting unit includes a second light emitter being positioned in said housing, said second light emitter being directed upwardly toward said passageway wherein said second light emitter is configured to emit ultraviolet light onto a bottom surface of the paper currency, said second light emitter being aligned with said first light emitter.

10. The assembly according to claim 1, wherein:
said roller unit includes a pair of first motors and a pair of second motors;
said disinfecting unit includes a first light emitter and a second light emitter; and
said control unit comprises a control circuit being positioned in said housing, said control circuit being electrically coupled to each of said first motors, said second motors, said first light emitter and said second light emitter, said control circuit receiving a disinfect input, each of said first motors, said second motors, said first light emitter and said second light emitter being turned on when said control circuit receives said disinfect input.

11. The assembly according to claim 10, wherein said control unit includes a touch screen being coupled to an angled wall of said housing wherein said touch screen is configured to be manipulated by the user, said touch screen being electrically coupled to said control circuit, said touch screen displaying operational indicia to facilitate the user to control operational parameters of said control circuit.

12. The assembly according to claim 11, wherein said control unit includes a power cord being coupled to and extending away from said housing, said power cord being electrically coupled to said control circuit, said power cord having a distal end with respect to said housing, said power cord having a male plug being electrically coupled to a power source comprising a female electrical outlet.

13. A currency disinfecting assembly for disinfecting paper currency, said assembly comprising:
a housing having an entry extending therein and an exit extending therein wherein said entry is configured to receive paper currency and said exit is configured to dispense the paper currency, said housing having a top wall, a front wall, and an angled wall sloping between said front wall and said top wall, said housing having a first lateral wall and a second lateral wall, said entry extending through said top wall, said exit extending through said front wall;
a chute being coupled to said front wall of said housing, said chute being aligned with said exit wherein said chute is configured to dispense the paper currency;
a roller unit being positioned in said housing, said roller unit being positioned between said entry and said exit Wherein said roller unit is configured to engage the paper currency, said roller unit being actuatable in a rolling condition wherein said roller unit is configured to transport the paper currency between said entry and said exit, said roller unit comprising:
a passageway being integrated into said housing, said passageway extending between said entry and said exit wherein said passageway is configured to transport the paper currency;
a pair of first rollers, each of said first rollers being rotatably positioned in said housing, each of said first rollers extending between said first lateral wall and said second lateral wall, each of said first rollers being positioned on opposing sides of said passageway from each other wherein each of said first rollers is configured to frictionally engage the paper currency, each of said first rollers being positioned closer to said entry than said exit;
a pair of first motors, each of said first motors being coupled to a respective one of said first rollers, each of said first motors rotating said respective first roller in a first direction when said first motors are turned on for transporting the paper currency through said passageway;
a pair of second rollers, each of said second rollers being rotatably positioned in said housing, each of said second rollers extending between said first lateral wall and said second lateral wall, each of said second rollers being positioned on opposing sides of said passageway from each other wherein each of said second rollers is configured to frictionally engage the paper currency, each of said second rollers being positioned closer to said exit than said entry; and
a pair of second motors, each of said second motors being coupled to a respective one of said second rollers, each of said second motors rotating said respective second roller in a first direction when said second motors are turned on for transporting the paper currency through said passageway;
a disinfecting unit being integrated into said housing, said disinfecting unit emitting electromagnetic radiation wherein said disinfecting unit is configured to kill bacteria, said disinfecting unit being including a plurality of emitters each being directed toward opposing sides of said roller unit wherein said disinfecting unit is configured to disinfect both sides of the paper currency as the paper currency is transported through said housing, said disinfecting unit being positioned and directed towards said roller unit adjacent to said exit of said housing wherein said disinfecting unit is configured for killing bacteria immediately prior to the paper currency being dispensed through said exit of said housing, said disinfecting unit comprising:
a first light emitter being positioned in said housing, said first light emitter being directed downwardly toward said passageway wherein said first light emitter is configured to emit ultraviolet light onto a top surface of the paper currency for sterilizing the top surface of the paper currency, said first light emitter being positioned between said second rollers and said exit in said housing; and
a second light emitter being positioned in said housing, said second light emitter being directed upwardly toward said passageway wherein said second light emitter is configured to emit ultraviolet light onto a bottom surface of the paper currency, said second light emitter being aligned with said first light emitter; and
a control unit being coupled to said housing wherein said control unit is configured to be manipulated by a user, said control unit being in communication with said roller unit and said disinfecting unit, said control unit turning on each of said roller unit and said disinfecting unit wherein said control unit is configured to facilitate the user to sterilize their paper currency, said control unit comprising:
a control circuit being positioned in said housing, said control circuit being electrically coupled to each of said first motors, said second motors, said first light emitter and said second light emitter, said control circuit receiving a disinfect input, each of said first motors, said second motors, said first light emitter and said second light emitter being turned on when said control circuit receives said disinfect input;
a touch screen being coupled to said angled wall of said housing wherein said touch screen is configured to be manipulated by the user, said touch screen being electrically coupled to said control circuit, said touch screen displaying operational indicia to facilitate the user to control operational parameters of said control circuit; and
a power cord being coupled to and extending away from said housing, said power cord being electrically coupled to said control circuit, said power cord having a distal end with respect to said housing, said power cord having a male plug being electrically coupled to a power source comprising a female electrical outlet.

\* \* \* \* \*